Nov. 26, 1963
C. FISCHER
GLADIOLUS PLANT
Filed July 5, 1962
Plant Pat. 2,316
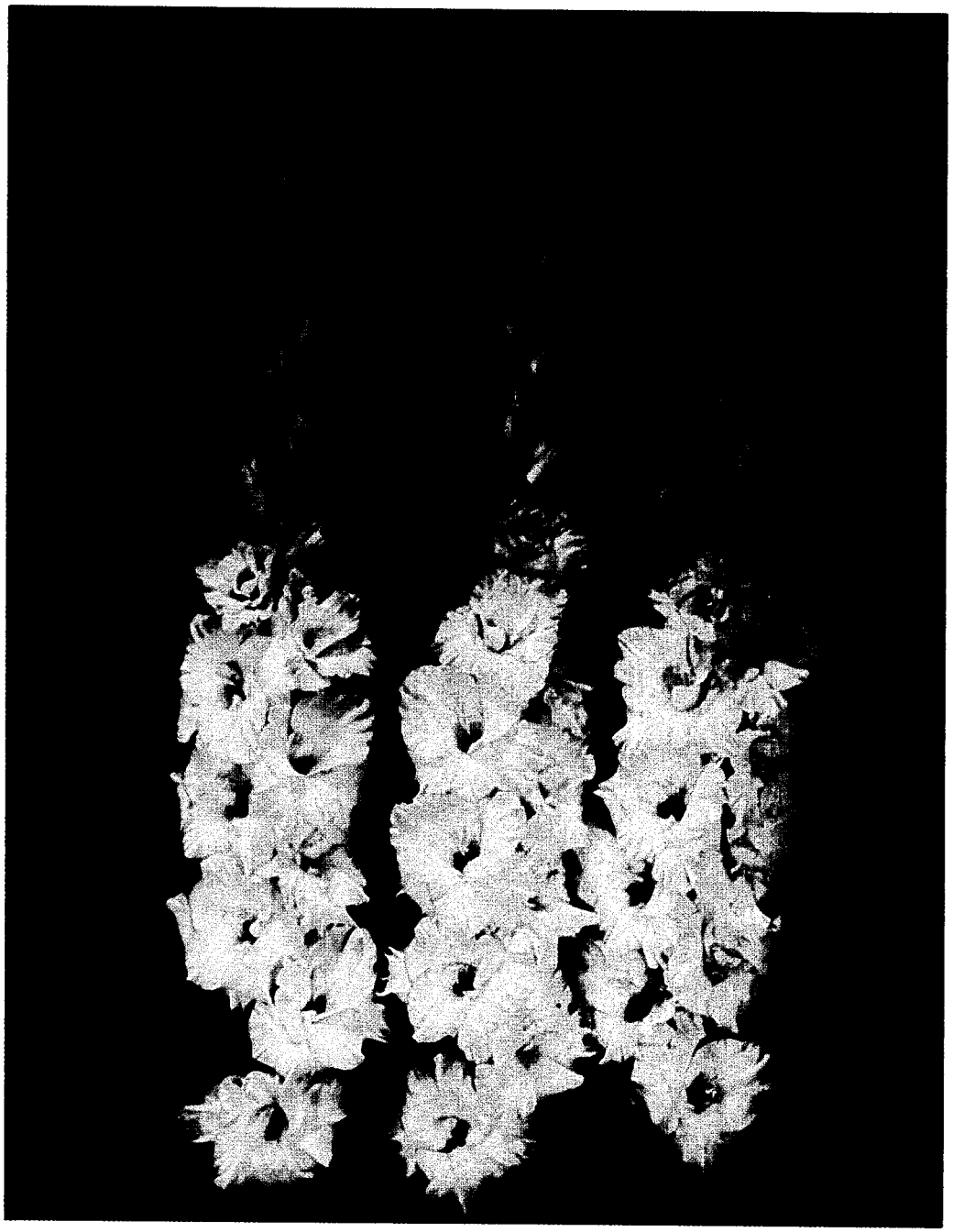
Inventor
Carl Fischer
By: Robb & Robb
Attorneys United States Patent Office Plant Pat. 2,316

Patented Nov. 26, 1963

2,316

GLADIOLUS PLANT

Carl Fischer, St. Charles, Minn., assignor to Imperial Flowers Limited, Leamington, Ontario, Canada, a corporation of Canada Filed July 5, 1962, Ser. No. 207,830
1 Claim. (Cl. Plt.—85)

The present invention relates to a new and distinct variety of gladiolus plant which was originated by me by crossing two unnamed and unpatented gladiolus varieties of unidentified parentage, said cross having been made by me by manual cross pollination as performed in my outdoor breeding fields at St. Charles, Minnesota.

As a result of this breeding, I have produced a new and improved gladiolus variety which is distinguished from its parents, as well as from all other varieties of which I am aware, as evidenced by the following unique combination of features which are outstanding therein:

(1) Prolific propagation;
(2) Heavy flower petal substance;
(3) Extreme ruffling of the flower petals;
(4) The ability to open well from tight buds;
(5) A distinctive and attractive luminescent Empire Rose general color tonality of the flowers, combined with Yellow colored flower throat and midribs, with a Deep Pink picotee pencilled on the edges of the flower petals; and
(6) Good color retention of the flowers.

My new variety resembles the variety known as "Frivolity" (unpatented) more than any other, but differs principally therefrom by being more prolific; healthier; the production of longer flower heads; the production of more buds; a habit of opening better from tight buds; opening of more florets at one time; more buds showing color at one time; a more intensely ruffled flower form; and a much heavier flower petal substance.

Asexual reproduction of my new variety by cormels through several generations, as performed by me at St. Charles, Minnesota, shows that the foregoing characteristics and distinctions come true to form and are established and transmitted through succeeding propagations.

The accompanying drawing shows several typical specimen flower spikes of my new variety, with the flowers in different stages of development ranging from closed buds through partially open buds to fully open flowers, as depicted in color as nearly true as it is reasonably possible to make the same in a color illustration of this character.

The following is a detailed description of my new variety, with color terminology in accordance with the Horticultural Colour Charts issued by the British Colour Council and the Royal Horticulrtural Society, except where general color terms of ordinary dictionary significance are obvious:

Locality where grown and observed: St. Charles, Minnesota.

Propagation: Holds its distinguishing characteristics through succeeding propagations by plantings derived from cormels.

*Plant*

Growth: Extremely vigorous; prolific propagator; blossom spike attains height ranging from 65 inches to 68 inches.

Blooming habit: Mid-season bloomer in the Northern latitudes of the United States; comes into bloom from large bulbs in from 75 to 80 days; bears from 20 to 22 buds, with from 7 to 9 buds opening at one time and with 8 or 9 buds showing color.

Stems: Tall; strong.
*Diameter at base.*—From ½ inch to ¾ inch.
*Color (just above the bulb).*—Roseine Purple, Plate 629/1.

Foliage: Leaves average 1½ inches wide and attain height of about 44 inches; inside leaves are upright, but outside leaves are slightly drooping. Color—healthy green.

Disease resistance: Unusually resistant to Fusarium yellows, Sclerotina dry rot and Septoria leaf spot, as determined by comparison with other varieties grown in my fields near St. Charles, Minnesota, in irrigated black loam soil.

Corms (bulbs): Heavy; plump; well-husked, with husks having purplish cast ranging from Solferino Purple, Plate 26/2, to Solferino Purple, Plate 26/3, and sometimes lighter.
*Color of flesh.*—Tinted with Solferino Purple, Plate 26/3.
*Size.*—Average 2 inches in diameter from adult plants.

*Flower*

Spike: Consists of from 20 to 22 buds, with from 7 to 9 buds opening at once and 8 or 9 buds showing color.

Bud:
*Size.*—From 3 inches to 3½ inches long when opening.
*Opening.*—Opens well and comparable to the best varieties.

Flower:
*Arrangement.*—Florets are semi-formally arranged on stem and almost always face forward.
*Size.*—Individual florets average from 5 inches to 5½ inches in diameter, with upper blooms being progressively smaller.
*Form.*—Florets are very round and unusually broad; open wide; extremely ruffled; recurved; somewhat needlepointed.
*Keeping qualities.*—Good; comparable to the best of all gladiolus varieties.

Petals:
*Shape.*—Broad; round; ruffled; recurved; somewhat needlepointed.
*Size.*—Outer petals—about 2½ inches wide. Lip petal—about 1½ inches wide.
*Aspect.*—Extremely heavy substance; smooth surface; leathery; extremely ruffled.
*Fragrance.*—None.
*Color.*—Basic color is Empire Rose, Plate 621/3, with throat blotch of Naples Yellow, Plate 403 and midribs of Naples Yellow, Plate 403/3, and with Deep Pink (Empire Rose) picotee pencilled on the edges of the petals.

*Reproductive Organs*

Stamens: Color—cream, with a faint lavender edging.
Pistils: Color—cream.

I claim:

A new and distinct variety of gladiolus plant, substantially as herein shown and described, characterized particularly as to novelty by the unique combination of prolific propagation, heavy flower petal substance, extreme ruffling of the flowers, the ability to open well from tight buds, a distinctive and attractive luminescent Empire Rose general color tonality of the flowers, said flowers having Yellow throats and midribs, and having a Deep Pink (Empire Rose) picotee pencilled on the edges of the petals, and good color retention of the flowers.

No references cited.